United States Patent
Schliephake et al.

(10) Patent No.: US 6,958,414 B2
(45) Date of Patent: Oct. 25, 2005

(54) PREPARATION OF AT LEAST ONE ORGANIC COMPOUND BY HETEROGENEOUSLY CATALYZED PARTIAL GAS-PHASE OXIDATION

(75) Inventors: Volker Schliephake, Schifferstadt (DE); Ulrich Hammon, Mannheim (DE); Ernst Lang, Wachenheim (DE); Carl-Ludwig Krüger, Ellerstadt (DE); Jürgen Schröder, Ludwigshafen (DE); Klaus Joachim Müller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 18 days.

(21) Appl. No.: 10/667,782

(22) Filed: Sep. 23, 2003

(65) Prior Publication Data

US 2004/0116730 A1 Jun. 17, 2004

(30) Foreign Application Priority Data

Dec. 16, 2002 (DE) .......................... 102 59 023

(51) Int. Cl.$^7$ ............................................ C07C 51/16
(52) U.S. Cl. ................. 562/545; 562/544; 562/542; 562/543; 562/598
(58) Field of Search ................. 562/510, 512, 562/523, 524, 256, 531, 532, 534, 555, 537, 538, 542, 543, 544, 545, 549; 568/924, 943

(56) References Cited

U.S. PATENT DOCUMENTS

| 3,119,837 A | 1/1964 | Kingsley et al. |
|---|---|---|
| 3,702,259 A | 11/1972 | Nielsen |
| 3,799,866 A | 3/1974 | Felice et al. |
| 3,956,377 A | 5/1976 | Dolhyj et al. |
| 4,077,912 A | 3/1978 | Dolhyj et al. |
| 4,105,744 A | 8/1978 | Erdoess et al. |
| 4,408,079 A | 10/1983 | Merger et al. |
| 4,496,770 A | 1/1985 | Duembgen et al. |
| 5,173,468 A | 12/1992 | Boehning et al. |
| 5,221,767 A | 6/1993 | Boehning et al. |
| 5,231,226 A | 7/1993 | Hammon et al. |

(Continued)

FOREIGN PATENT DOCUMENTS

| DE | 1 254 137 | 11/1967 |
|---|---|---|
| DE | 2 159 346 | 6/1972 |
| DE | 2 106 796 | 8/1972 |
| DE | 2 351 151 | 4/1974 |
| DE | 25 26 238 | 1/1976 |
| DE | 1 464 198 | 2/1977 |
| DE | 40 22 212 | 1/1992 |
| DE | 41 32 263 | 4/1993 |
| DE | 41 32 684 | 4/1993 |
| DE | 43 11 608 | 12/1994 |
| DE | 195 01 325 | 7/1996 |
| DE | 199 02 562 | 7/2000 |
| DE | 199 10 506 | 9/2000 |
| DE | 199 10 508 | 9/2000 |
| DE | 199 27 624 | 12/2000 |
| DE | 199 48 248 | 4/2001 |

(Continued)

OTHER PUBLICATIONS

H. Beyer, et al., Lehrbouch Der Organischen Chemie, vol. 17, p. 261, 1973.

Primary Examiner—Johann Richter
Assistant Examiner—Karl Puttlitz
(74) Attorney, Agent, or Firm—Oblon, Spivak, McClelland, Maier & Neustadt, P.C.

(57) ABSTRACT

Organic compounds are prepared by heterogeneously catalyzed partial gas-phase oxidation of precursor compounds by a process in which a portion of the reaction gas starting mixture is brought from a low initial pressure to a higher final pressure by means of a radial compressor.

16 Claims, 5 Drawing Sheets

U.S. PATENT DOCUMENTS

| | | | |
|---|---|---|---|
| 5,245,093 A | * | 9/1993 | Ember .................. 585/266 |
| 5,264,625 A | | 11/1993 | Hammon et al. |
| 5,637,222 A | | 6/1997 | Herbst et al. |
| 5,668,077 A | | 9/1997 | Klopries et al. |
| 5,734,068 A | | 3/1998 | Klopries et al. |
| 6,348,638 B1 | | 2/2002 | Schliephake et al. |
| 6,395,936 B1 | | 5/2002 | Arnold et al. |
| 6,403,829 B1 | | 6/2002 | Unverricht et al. |
| 6,410,785 B1 | | 6/2002 | Zehner et al. |
| 6,433,222 B1 | * | 8/2002 | Eck et al. .................. 562/600 |
| 2003/0181762 A1 | | 9/2003 | Machhamer et al. |
| 2003/0187298 A1 | | 10/2003 | Borgmeier et al. |

FOREIGN PATENT DOCUMENTS

| | | |
|---|---|---|
| DE | 199 48 421 | 4/2001 |
| DE | 100 28 582 | 12/2001 |
| DE | 100 46 672 | 3/2002 |
| DE | 101 31 297 | 1/2003 |
| EP | 0 058 927 | 9/1982 |
| EP | 0 092 097 | 10/1983 |
| EP | 0 372 972 | 6/1990 |
| EP | 0 529 853 | 3/1993 |
| EP | 0 608 838 | 8/1994 |
| EP | 0 695 736 | 2/1996 |
| EP | 0 778 255 | 6/1997 |
| EP | 0 925 272 | 6/1999 |
| EP | 1 041 062 | 10/2000 |
| EP | 1 090 684 | 4/2001 |
| EP | 1 180 508 | 2/2002 |
| EP | 0 990 636 | 9/2003 |
| GB | 1 291 354 | 10/1972 |
| WO | WO 97/48669 | 12/1997 |
| WO | WO 01/96270 | 12/2001 |
| WO | WO 03/11804 | 2/2003 |

* cited by examiner

PREPARATION OF AT LEAST ONE ORGANIC COMPOUND BY HETEROGENEOUSLY CATALYZED PARTIAL GAS-PHASE OXIDATION

CROSS-REFERENCES TO RELATED APPLICATIONS

Not applicable.

STATEMENT REGARDING FEDERALLY SPONSORED RESEARCH OR DEVELOPMENT

Not applicable.

INCORPORATION-BY-REFERENCE TO MATERIAL SUBMITTED ON A COMPACT DISC

Not applicable.

BACKGROUND OF THE INVENTION (1) Field of the Invention

The present invention relates to a process for the preparation of at least one organic compound by heterogeneously catalyzed partial gas-phase oxidation of at least one organic precursor compound in a reactor loaded with catalyst, in which at least one portion of the components of the reaction gas starting mixture is brought from a low initial pressure to a higher final pressure by means of a compressor.

Here, a complete oxidation of an organic compound with molecular oxygen is understood as meaning that the organic compound is converted under the reactive action of molecular oxygen so that all the carbon contained in the organic compound is converted into oxides of carbon and all the hydrogen contained in the organic compound is converted into oxides of hydrogen. All reactions of an organic compound under the reactive action of molecular oxygen which differ therefrom are summarized here as partial oxidation of an organic compound.

In particular, partial oxidations are to be understood here as meaning those reactions of organic compounds under the reactive action of molecular oxygen in which the organic compound to be partially oxidized contains at least one chemically bonded oxygen atom more after the end of the reaction than before the partial oxidation was carried out.

Here, an ethylenically unsaturated double bond is to be understood as meaning a chemical double bond between two carbon atoms which either may occur singly in the molecule, may be isolated from other multiple bonds or may be conjugated or condensed with other multiple bonds.

In this document, diluent gases which are substantially inert under the conditions of the heterogeneously catalyzed gas-phase partial oxidation should be in particular those diluent gases whose components remain more than 95, preferably more than 99, mol % unchanged under the conditions of the heterogeneously catalyzed partial gas-phase oxidation, when each component is considered by itself.

It is generally known that numerous key chemicals can be produced by heterogeneously catalyzed partial oxidation of different organic precursor compounds with molecular oxygen in the gas phase.

(2) Description of Related Art Including Information Disclosed Under 37 C.F.R. §1.97 and 1.98.

The conversion of n-butane into maleic anhydride, the conversion of propylene into acrolein and/or acrylic acid (cf. for example DE-A 2351151), the conversion of tert-butanol, isobutene, isobutane, isobutyraldehyde or the methyl ether of tert-butanol into methacrolein and/or methacrylic acid (cf. for example DE-A 2526238, EP-A 92097, EP-A 58927, DE-A 4132263, DE-A 4132684 and DE-A 4022212), the conversion of acrolein into acrylic acid, the conversion of methacrolein into methacrylic acid (cf. for example DE-A 2526238), the conversion of butadiene into maleic anhydride (cf. for example DE-A 2106796 and DE-A 1624921), the conversion of n-butane into maleic anhydride (cf. for example GB-A 1464198 and GB-A 1291354), the conversion of ethylene into ethylene oxide or of propylene into propylene oxide (cf. for example DE-AS 1254137, DE-A 2159346, EP-A 372972, WO 89/0710, DE-A 4311608 and Beyer, Lehrbuch derorganischen Chemie, 17th edition (1973), Hirzel Verlag Stuttgart, page 261), the conversion of propylene and/or acrolein into acrylonitrile (cf. for example DE-A 2351151), the conversion of isobutene and/or methacrolein into methacrylonitrile (i.e. in this document, the term partial oxidation is also intended to include partial ammoxidation, i.e. a partial oxidation in the presence of ammonia), the oxidative dehydrogenation of hydrocarbons (cf. for example DE-A 2351151), the conversion of propane into acrylonitrile or into acrolein and/or acrylic acid (cf. for example DE-A 10131297, EP-A 1090684, EP-A 608838, DE-A 10046672, EP-A 529853, WO 01/96270 and DE-A 10028582), etc. may be mentioned by way of example.

The catalysts to be used for such reactions are usually solids.

Particularly frequently, the catalysts to be used are solid oxide materials or noble metals (e.g. Ag). In addition to oxygen, the catalytically active oxide material may contain only one other element or more than one other element (multielement oxide materials). Particularly frequently used catalytically active oxide materials are those which comprise more than one metallic, in particular transition metal, element. In this case, the term multimetal oxide material is used.

Owing to the usually pronounced exothermic character of most heterogeneously catalyzed gas-phase partial oxidations of organic compounds with molecular oxygen, the reactants are usually diluted with a gas which is substantially inert under the conditions of the gas-phase catalytic partial oxidation and which, with its heat capacity, is capable of absorbing the liberated heat of reaction and advantageously influencing the reaction rate.

One of the most frequently used inert diluent gases is molecular nitrogen, which is always automatically used whenever air is used as an oxygen source for the heterogeneously catalyzed gas-phase partial oxidation.

Another inert diluent gas which is often used, owing to its general availability, is steam. Recycle gas is also often used as inert diluent gas (cf. for example EP-A 1180508). Recycle gas is defined as the residual gas which remains when the desired product has been separated off more or less selectively (for example by absorption in a suitable solvent) from the product gas mixture after a one-stage or multistage (in the multistage heterogeneously catalyzed gas-phase partial oxidation of organic compounds, the gas-phase partial oxidation, in contrast to the one-stage heterogeneously catalyzed gas-phase partial oxidation, is carried out not in one reactor but in at least two reactors connected in series, it being possible to add oxidizing agents between successive reactors; the multistage character is used in particular when the partial oxidation takes place in successive steps; in these cases, it is frequently expedient to adapt both the catalyst and the other reaction conditions to the respective reaction step in an optimum manner and to carry out the reaction step in a separate reactor, in a separate reaction stage; however, it can also be used if, for reasons relating to heat removal or further reasons (cf. for example DE-A 19902562), the reaction is spread over a plurality of reactors connected in series; an example of a heterogeneously catalyzed gas-phase partial oxidation frequently carried out in two stages is the partial oxidation of propylene to acrylic acid; the propylene is oxidized to acrolein in the first reaction stage, and the acrolein is oxidized to acrylic acid in the second reaction stage; methacrylic acid production is also frequently carried out in a corresponding manner in two stages, generally starting from isobutene; both abovementioned partial oxidations can, however, also be carried out in one stage (both steps in one reactor) when suitable catalyst loads are used) heterogeneously catalyzed gas-phase partial oxidation of at least one organic compound. As a rule, it predominantly comprises the inert diluent gases used for the partial oxidation and steam usually formed as a byproduct in the partial oxidation and oxides of carbon which are formed by undesired complete secondary oxidation. In some cases, it also contains small amounts of oxygen not consumed in the partial oxidation (residual oxygen) and/or of unconverted organic starting compounds. Usually, only a proportion of the residual gas is used as recycle gas. The remaining amount of residual gas is usually incinerated.

A heterogeneously catalyzed partial gas-phase oxidation is usually carried out over a fixed catalyst bed or in a fluidized catalyst bed.

For this purpose, the reaction gas starting mixture, which substantially comprises the at least one organic precursor compound, molecular oxygen (if required, ammonia in the case of an ammoxidation) and inert diluent gas (including, if required, recycle gas), is as a rule passed through the catalyst load at elevated temperatures (as a rule a few hundred ° C., usually from 100 to 600° C.). The chemical reaction takes place during the period of contact with the catalyst surface.

As stated above in the case of the formation of recycle gas, owing to numerous simultaneous and subsequent reactions taking place in the course of the catalytic gas-phase partial oxidation and owing to the inert diluent gases generally present (in certain circumstances, the at least one organic precursor compound can also act as an inert diluent gas, i.e. when it is present in excess in the reaction gas starting mixture relative to the molecular oxygen contained therein), a heterogeneously catalyzed partial gas-phase oxidation gives not a pure organic desired compound but a reaction gas mixture from which the desired product has to be isolated.

If the region of the gas-phase oxidation forms the actual reaction zone, the product gas mixture is usually fed to a working-up zone for isolating the desired product, in which zone this isolation is effected.

Typically (for example in the case of acrylic acid and in the case of methacrylic acid), the isolation of the desired product from the product gas mixture is effected by extraction, fractional condensation and/or rectification methods in separation columns which contain internals with separation activity and through which the product gas mixture is passed (cf. for example EP-A 1 041 062, EP-A 778 255, EP-A 695 736, DE-A 19 501 325 and EP-A 925 272). As described above, the remaining residual gas is concomitantly used, if required, as recycle gas for diluting the reaction gas starting mixture.

For transporting the reaction mixture through the catalyst load of the heterogeneously catalyzed partial gas-phase oxidation and through the subsequent working-up, a pressure difference between reactor entrance and residual gas exit is necessary.

This pressure difference is usually produced in practice by bringing the reaction gas starting mixture, before it enters the oxidation reactor, to a pressure which is higher than the ambient air pressure. These pressures are typically from 0.2 to 5, frequently from 0.5 to 4.5, often from 1 or 2 to 4, bar gage pressure (excess pressure relative to customary atmospheric pressure). High pressures are required in particular when the gas volume flow to be transported is large (for example in high-load procedures, as described in DE-A 19927624, DE-A 19948248, DE-A 19948241, DE-A 19910508 and DE A 19910506), since the latter also requires a greater pressure drop for transport through the catalyst load, if required intermediate and/or downstream condensers loaded with packings, and the working-up apparatuses, for a given reactor and given working-up apparatus.

While the organic precursor compound to be partially oxidized is frequently stored in liquid form in practice it is generally gaseous at atmospheric pressure and room temperature, simple vaporization is as a rule sufficient for bringing the organic precursor compound to be partially oxidized to the reactor entrance pressure. Steam to be concomitantly used as inert diluent gas is generally available from a very wide range of sources, likewise at sufficient superatmospheric pressure.

As a rule, however, this is not true at least for the oxygen source (e.g. air or oxygen-enriched air), the recycle gas (it usually has a pressure equal to the reactor entrance pressure minus the pressure drop on the way through the oxidation zone and through the working-up zone) and any other inert diluent gases.

In practice, it is therefore usually necessary to bring at least a portion of the components of the reaction gas starting mixture from a low initial pressure to a higher final pressure (generally the reactor entrance pressure) by means of a compressor (cf. for example FIG. 1 of EP-A 990 636).

The compression of these components (e.g. air as the oxygen source and recycle gas as the diluent gas source) can be carried out in spatially separate compressors or in a single compressor.

The portions of the reaction gas starting mixture which originate from various sources and are substantially present at (have substantially been brought to) reactor entrance pressure are transported in separate pipes and are then generally first mixed in a mixer, for example a static mixer (space containing internals which generate turbulence) and then, if necessary, heated to the entrance temperature and then fed to the oxidation reactor (the entrance of the individual gases into the pipe leading to the static mixer is frequently expediently chosen so that the formation of explosive mixtures is avoided (in the case of a partial oxidation of propylene to, for example, acrolein and/or acrylic acid, this entry sequence could expediently be, for example, first recycle gas and/or steam, then crude propene and then air)).

The fact that at least one chemical compound having at least one ethylenically unsaturated double bond is involved in most heterogeneously catalyzed partial gas-phase oxidations (for example in all those cited at the outset) is problematic.

This may be, for example, the organic precursor compound to be partially oxidized (e.g. butadiene, propylene, isobutene, acrolein, methacrolein) or the desired product (e.g. acrylic acid, methacrylic acid, acrylonitrile, methacrylonitrile) or an intermediate.

Particularly recycle gas contains, as a rule, at least one chemical compound having at least one ethylenically unsaturated double bond.

This is not entirely uncritical in that chemical compounds having at least one ethylenically unsaturated double bond generally have a pronounced tendency to undesired free radical polymerization. This tendency to polymerization is further increased in the condensed phase and can be additionally promoted by impurities contained therein, which is why gases which are to be compressed and which have components containing at least one ethylenically unsaturated group are frequently heated before they are fed to a compressor (cf. page 6, lines 5 and 6, of EP-A 990 636), in order substantially to rule out undesired droplet formation during compression.

During continuous operation of a production plant, however, neither such undesired droplet formation nor polymerization-promoting impurities can be fully excluded.

Possible solid and/or liquid impurities in the various components of the reaction gas starting mixture (for example, dust in the air used as an oxygen source), which may be deposited, constitute a further problem area.

In principle, a very wide range of compressor types can be used for compressing gases. Displacement compressors (e.g. reciprocal piston compressors, screw compressors and rotary piston compressors), flow compressors (e.g. turbo compressors, centrifugal compressors, axial compressors and radial compressors) and jet compressors may be mentioned by way of example.

BRIEF SUMMARY OF THE INVENTION

In view of the abovementioned facts, it is an object of the present invention to provide a process for the preparation of at least one organic compound by heterogeneously catalyzed partial gas-phase oxidation of at least one organic precursor compound in a reactor loaded with catalyst, in which at least one portion of the components of the reaction gas starting mixture is brought from a low initial pressure to a higher final pressure by means of a compressor, and in which the compressor is chosen so that it can be operated substantially without being impaired by the problems described.

DETAILED DESCRIPTION OF THE INVENTION

We have found that this object is achieved by a process for the preparation of at least one organic compound by heterogeneously catalyzed partial gas-phase oxidation of at least one organic precursor compound in a reactor loaded with catalyst, in which at least one portion of the components of the reaction gas starting mixture is brought from a low initial pressure to a higher final pressure by means of a compressor, wherein the compressor used is a radial compressor.

The novel process is particularly suitable when the at least one portion of the components of the reaction gas starting mixture which is to be compressed contains at least one chemical compound having at least one ethylenically unsaturated double bond and/or air.

Figure 1:
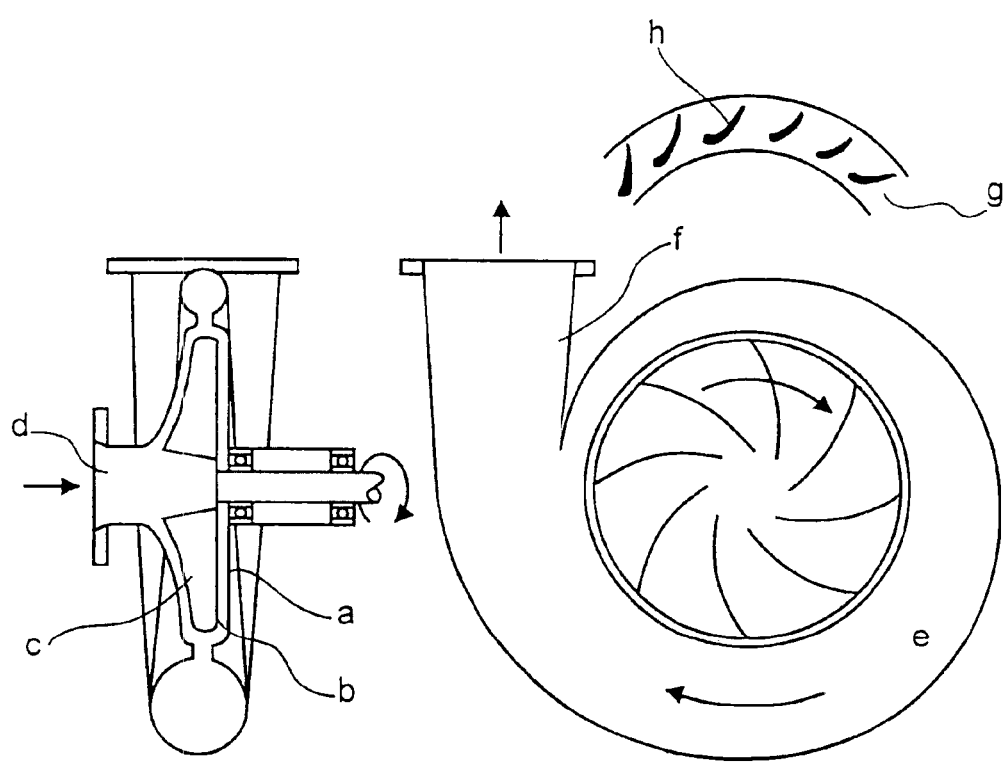
FIG. 1 shows a radial compressor of the present invention.
Figure 2:
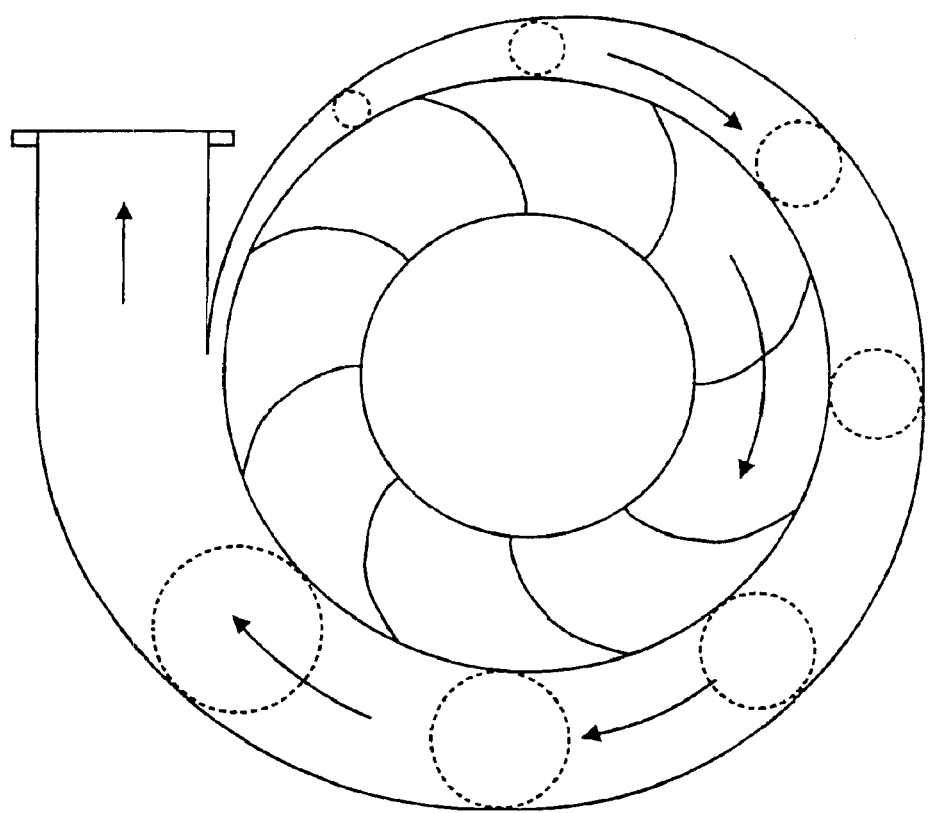
FIG. 2 shows another view of the radial compressor of the present invention.

The mode of operation of a radial compressor can be illustrated as follows (cf. FIG. 1). It consists in principle of a housing (a) and at least one rotor (b) which rotates therein and is provided with blades (c) (cf. also FIG. 4). The gas to be compressed enters axially through a suction nozzle (d). It is deflected radially outward with the centrifugal force of the rotating rotor (closed disk with blades) and thus accelerated to high velocity by the rotor. The function of the housing is to trap the gas and collect it so that it can be further transported through the pressure exits (f). The housing simultaneously has the function of converting kinetic energy into pressure. The fact that an increase in cross section reduces the velocity of the gas and thus effects a pressure increase is generally utilized for this purpose. Various designs of the housing are possible for increasing the cross section. In one-stage compressors or downstream of the last stage of multistage compressors, spiral housings are frequently used. The housing of this type encloses the rotor in spiral form (e). The cross section increases toward the pressure exit (cf. increasing radii of circles in FIG. 2). The gas flowing through is thus slowed down which implies a simultaneous pressure increase.

Figure 3:
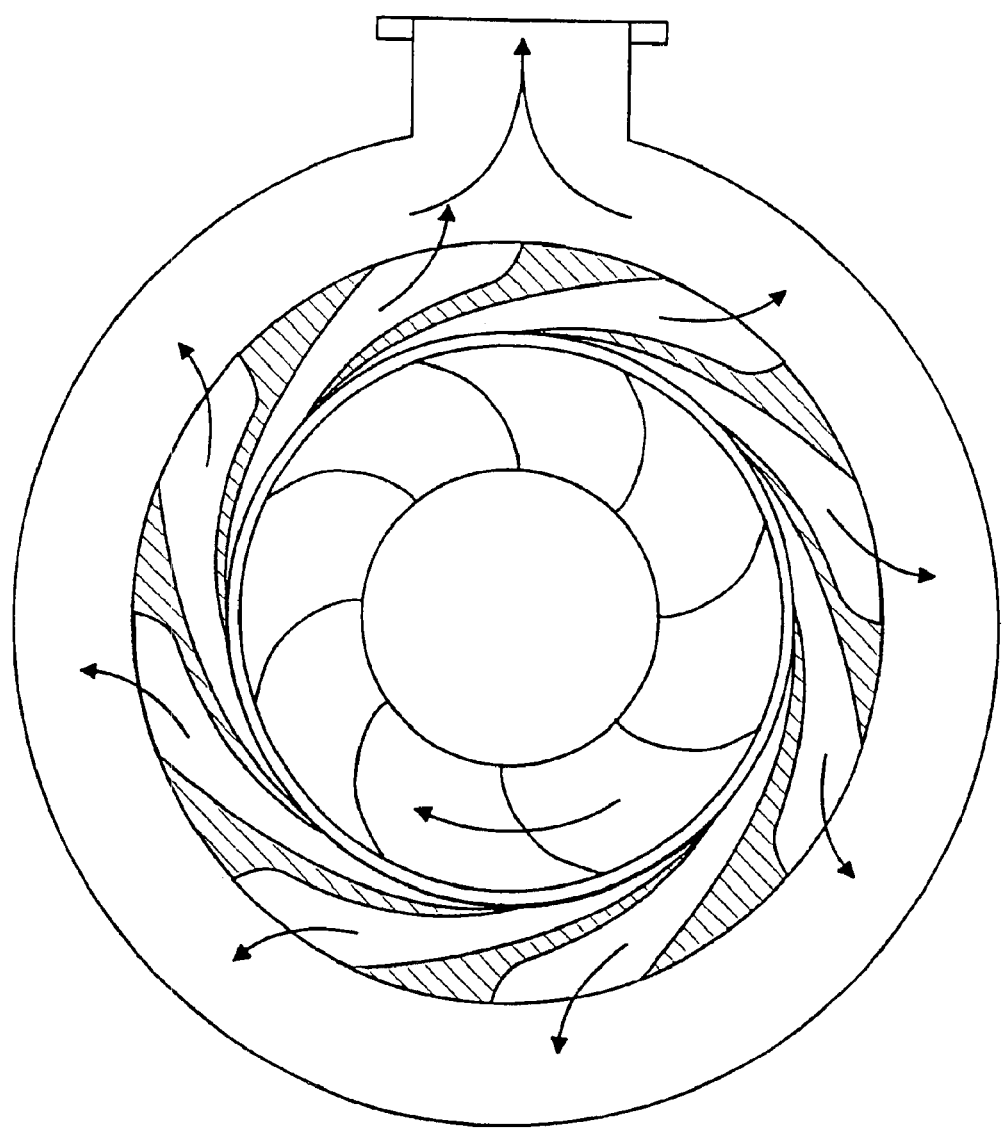
FIG. 3 shows another type of radial compressor of the present invention.

Instead of the spiral, it is also possible to use stators (g), particularly in the case of multistage compressors. The stator is installed in the housing and is in the form of an annular space. It encloses the rotor. Guide blades (h) which form channels with one another which widen continuously in an outward direction are arranged in the stator (FIG. 3). In this embodiment, the gas is not accelerated directly into the housing but first flows through the blade channels of the stator. Owing to the widening in the flow direction, they once again produce a decrease in the flow velocity and the consequent pressure build-up.

The direction of the stator channels is usually opposite to the direction of the rotor channels and, at the inner circumference of the stator, corresponds to the direction of the exit velocity of the transport gas from the rotor. A further function of the stator in the case of two-stage radial compressors is to collect the transport gas and convey it to the entrance of the second stage.

Figure 4:
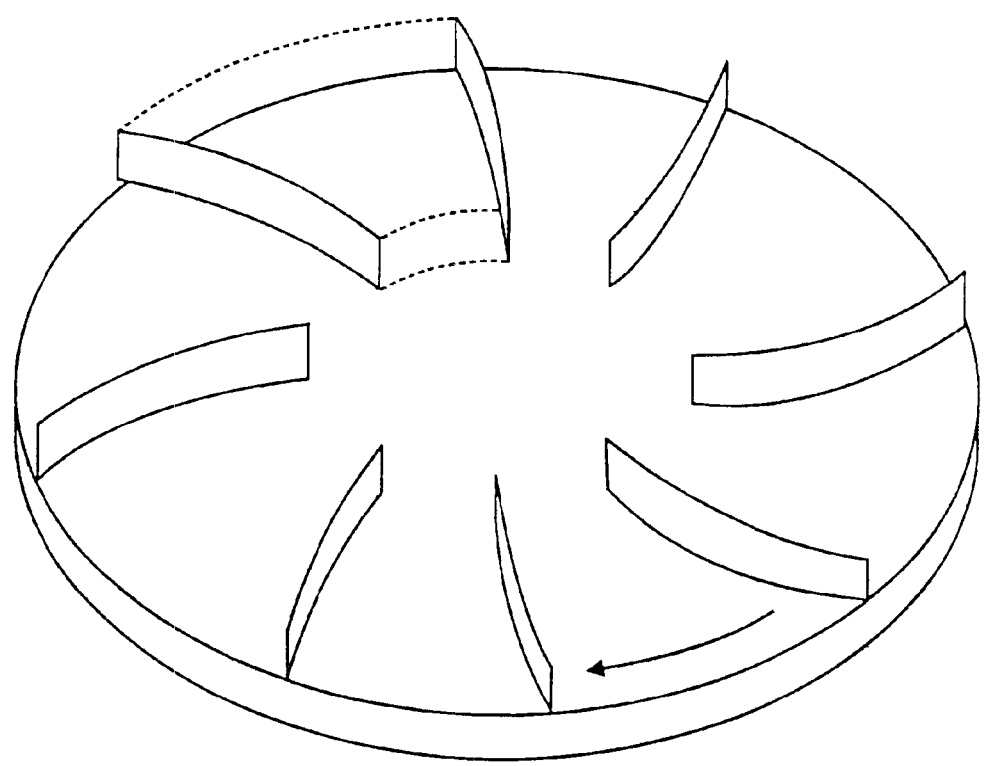
FIG. 4 shows an arrangement of the rotors in the radial compressor of the present invention.
Figure 5:
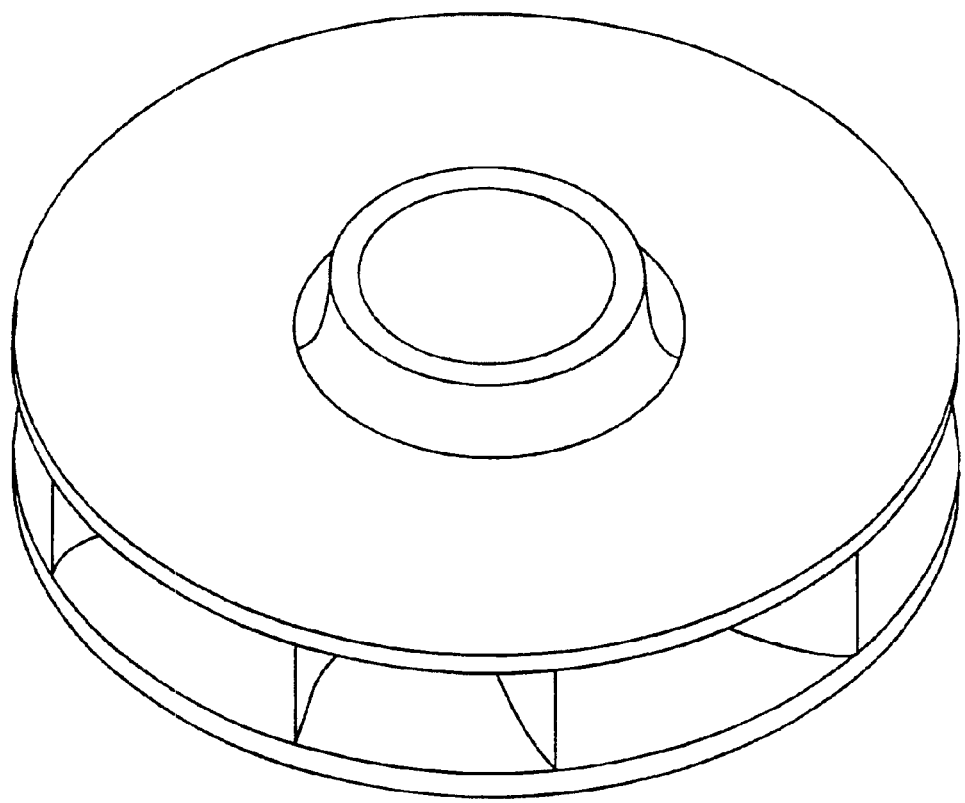
FIG. 5 shows another arrangement of rotors in the radial compressor of the present invention.

In contrast to the rotor according to FIG. 4, it is also possible to use rotors according to FIG. 5. Here, the blade channels are in principle simply covered by a second complete or partial disk (in the former case, it has an orifice in the middle).

It is of course also possible to use a combination of stator and spiral housing. This means that the transport gas is first collected in the stator before it can enter the spiral housing.

Whereas so far substantially only the actual compressor space has been discussed, the drive will also be discussed below. As a rule, the rotor is driven by directly coupled high-speed engines, such as electric motors, gas turbines, internal combustion engines or steam turbines. The coupling is usually effected by means of a drive shaft.

However, gear-type radial compressors are preferred according to the invention. In this case, rotor and engine are no longer directly coupled via a single drive shaft. Rather, rotational movement of the engine-driven drive shaft is transmitted via mechanical means (gear) to the compressor shaft or output shaft driving the rotor, the speeds of drive shaft and output shaft generally being different. The latter makes it possible to optimize the compressor efficiency (a predetermined amount of gas can be brought from the respective low initial pressure to the respective higher final pressure with minimized energy consumption). Rotors mounted on either one side or two sides are used. The latter are more complicated in design but are less sensitive to soiling.

Typical transport streams of the novel process are from 30 000 to 200 000 m$^3$(S.T.P.)/h. On the basis of the use of reactors and catalyst loads as described in the prior art, e.g. in DE-A 4431957 and in DE-A 4431949, transport streams of 100 000 m$^3$(S.T.P.)/h frequently correlate with applied reactor entrance pressures of about 2 bar gage pressure, volume flow rates of 200 000 m$^3$(S.T.P.)/h with applied reactor entrance pressures of about 3.3 bar gage pressure, volume flow rates of 50 000 m$^3$(S.T.P.)/h with applied reactor entrance pressures of about 1.7 bar gage pressure and volume flow rates of 30 000 m$^3$(S.T.P.)/h with applied reactor entrance pressures of about 200 mbar gage pressure.

Multistage radial compressors have a number of rotors connected in series which corresponds to the number of stages. In principle, it comprises a series of compressions. Typical according to the invention are 1- to 3-stage radial compressors. Since as a rule the resulting pressure increases with increasing rotor speed, a multistage radial compressor permits a rotor speed limitation relative to the desired final pressure. This rotor speed limitation is important in practice because, depending on the material used, maximum permissible rotor circumferential velocities must not be exceeded for safety reasons.

Instead of a radial compressor, it would also be possible to use an axial compressor for the novel process. These most closely resemble the radial compressors and differ from the former substantially only in that the rotor is replaced by a screw or a propeller or a propeller analog having a relatively large number of blades. Since in the case of the axial compressor no closed rotor disk but a sort of permeable arrangement of guide blades curved in a certain manner is present, the gas to be compressed is no longer deflected radially but flows in the axial direction through the optionally multistage screw or propeller arrangement. Usually, the rotating propellers transport the gas to be compressed through a narrowing space. After the last stage, a diffuser is usually present again for utilizing the exit energy.

In order to bring a predetermined transport stream from a predetermined initial pressure to a desired final pressure, axial compressors usually require higher speeds than radial compressors (assuming identical rotor diameters). As a result of detailed investigations, however, it has been found that axial compressors are less suitable for the novel process since polymeric deposits on the screws or propellers prematurely lead to out-of-true running and shaft oscillations.

Radial compressors preferred according to the invention are the gear-type turbo compressor of the type VK and single-shaft compressor MH4B, each from Siemens in Duisburg, Germany. Radial compressors having inlet vane guides or vane control are particularly preferred.

The novel process is of course also suitable for processes for heterogeneously catalyzed partial oxidation in which no chemical compound having at least one ethylenically unsaturated double bond is involved (e.g. xylene to phthalic anhydride).

The novel process is especially suitable for a two-stage catalytic gas-phase partial oxidation of propene with molecular oxygen to acrylic acid.

This gas-phase partial oxidation can be carried out, for example, as in the versions described in DE-A 10232748.

This means that the procedure for the first step, from propylene to acrolein, can be carried out, for example, in a one-zone fixed-bed reactor having a plurality of catalyst tubes, as described in DE-A 4431957. Air is expediently used as an oxygen source. The crude propylene to be used may be polymer grade propylene or chemical grade propylene, as is familiar to a person skilled in the art and described, for example, in DE-A 10232748. Recycle gas and/or steam is preferably present as inert diluent gas.

Usually, a propene:oxygen:inert gases (including steam) volume (I(S.T.P.)) ratio of 1:(1.0 to 3.0):(5 to 25) is employed.

The total space velocity is preferably from 1 500 to 4 000, frequently from 1 500 to 3 000, I(S.T.P.) per l per h. The propene space velocity is typically from 90 to 250, frequently from 90 to 150, I(S.T.P.) per l (catalyst load) per h.

For carrying out the second step, from acrolein to acrylic acid, the product gas mixture of the first stage can be fed directly to a further one-zone fixed-bed reactor having a plurality of catalyst tubes, if necessary after intermediate cooling and supply of secondary air, as described in DE-A 4431949.

As a rule, the feed gas mixture of such a second stage has the following composition: acrolein:oxygen:steam:inert gas volume ratio I(S.T.P.) of 1:(1 to 3):(0 to 20):(3 to 30)

The total space velocity is preferably from 1 000 to 4 000, frequently from 1 000 to 2 500, I(S.T.P.) per l per h. The acrolein space velocity is typically from 80 to 250, frequently from 80 to 170, I(S.T.P.) per l per h.

However, it would of course also be possible to use a tube-bundle reactor as described in DE-A 19836792 for both reaction stages.

The loading of the reaction tubes of the two stages with catalyst can be carried out, for example, as described in DE-A 4431957 and in DE-A 4431949.

It would, however, also be possible to carry out the first-stage loading according to EP-A 1005908 and the two-stage loading according to EP-A 1071507. Of course, loading can however also be effected as described in DE-A 10232748.

The novel process is particularly suitable for a heterogeneously catalyzed fixed-bed gas-phase partial oxidation of propene (with molecular oxygen; oxygen source is as a rule air) to acrylic acid, taking place in two successive steps, as described, for example, in EP-A 1106598, WO 00/53559, WO 00/53556, WO 00/53557, WO 00/93558 and WO 01/36364, the propene space velocity of the fixed catalyst bed for the first step from propene to acrolein being $\geq 135$ I (S.T.P.) per l per h and the acrolein space velocity of the fixed catalyst bed for the second step from acrolein to acrylic acid being $\geq 125$ I (S.T.P.) per l per h or $\geq 130$ I (S.T.P.) per l per h.

Frequently, the abovementioned propene space velocity is $\geq 140$ or $\geq 145$ or $\geq 150$ or $\geq 155$ or $>160$ I (S.T.P.) per l per h. In a corresponding manner, the abovementioned acrolein space velocity is then $\geq 130$ or $\geq 135$ or $\geq 140$ or $\geq 150$ I (S.T.P.) per l per h. Usually both abovementioned space velocities are $\leq 300$ or 250 or $\leq 200$ I (S.T.P.) per l per h.

The isolation of acrylic acid from the product gas mixture and the formation of recycle gas can be carried out, for example, as in EP-A 982287, EP-A 982289, DE-A 19924532, DE-A 10115277, DE-A 19606877, DE-A 19740252, DE-A 19627847, DE-A 10053086, EP-A 982288, DE-A 19627847, WO 97/48669 and EP-A 925272.

A typical recycle gas composition is:

0–0.1% by volume of other substances, e.g. biphenyl, diphenyl ether and/or dimethyl phthalate, >0–0.1% by volume of acrylic acid, >0–0.1% by volume of acrolein, 3–5% by volume of oxygen, 1–15% by volume of steam (frequently from 1 to 5% by volume), >0–3% by volume of carbon monoxide, >0–8% by volume of carbon dioxide, 0–2% by volume of propane, 0.1–0.5% by volume of propylene and 75–95% by volume of nitrogen.

The compression of the recycle gas and of the air can be carried out in two separate compressors which are driven by two separate motors or in two compressors which are driven by one motor or in a single compressor driven by a motor.

The novel process can, however, also be applied to all other heterogeneously catalyzed partial gas-phase oxidations which were mentioned at the outset. As a rule, the portion of the components of the reaction gas starting mixture to be compressed will contain from >0 to 0.5, frequently from 0.01 to 0.3, % by volume of at least one chemical compound having at least one ethylenically unsaturated double bond. The novel process is advantageous particularly when the latter is acrolein, acrylic acid, acrylonitrile, methacrolein, methacrylic acid and/or methacrylonitrile.

Example and comparative example (two-stage heterogeneously catalyzed partial gas-phase oxidation of propylene to acrylic acid)

a) EXAMPLE

The reaction gas starting mixture is composed of 5.4% by volume of chemical grade propylene, 52.5% by volume of air (primary air) and recycle gas as the remainder.

Dimensions of the catalyst tubes in both stages:

3 200 mm length, 25 mm internal diameter, 30 mm external diameter and 2.5 mm wall thickness.

1. Loading of Catalyst Tubes of the First Stage (In Direction of Gas Flow):

50 cm preliminary bed of steatite rings measuring 7 mm×7 mm×4 mm (external diameter×length×internal diameter);

100 cm catalyst bed comprising a homogeneous mixture of 30% by weight of steatite rings measuring 5 mm×3 mm×2 mm (external diameter×length×internal diameter) and 70% by weight of unsupported catalyst according to example 1 of DE-A 10046957; 170 cm catalyst bed comprising annular (5 mm×3 mm×2 mm=external diameter×length×internal diameter) of unsupported catalyst according to example 1 of DE-A 10046957.

Temperature of the surrounding salt bath: 337° C.

2. Intermediate Condenser

Indirect condenser which the product gas mixture leaves at 250° C. Compressed air (secondary air) at 140° C. is then mixed with said product gas mixture.

3. Loading of Catalyst Tube of the Second Stage (In Direction of Gas Flow):

20 cm preliminary bed of steatite rings measuring 7 mm×7 mm×4 mm (external diameter×length×internal diameter).

100 cm catalyst bed comprising a homogeneous mixture of 30% by weight of steatite rings measuring 7 mm×3 mm×4 mm (external diameter×length ×internal diameter) and 70% by weight of a coated catalyst according to preparation example 5 of DE-A 10046928;

200 cm catalyst bed comprising annular (about 7 mm×3 mm×4 mm) coated catalyst according to preparation example 5 of DE-A 10046928.

Temperature of the surrounding salt bath: 265° C.

According to an embodiment of DE-A 19501325, the acrylic acid is separated off by absorption from the product gas mixture of the second stage by means of a mixture containing 57.4% by weight of diphenyl ether, 20.7% by weight of biphenyl and 20% by weight of o-dimethyl phthalate and is further purified to give a crude acrylic acid having a purity of ≧99.3% by weight. The remaining unabsorbed product gas is further cooled in order to separate off the condensable part of the low-boiling secondary components therefrom, in particular water, formaldehyde and acetic acid, by condensation in a dilute acid quench according to EP-A 925272. The remaining gas stream forms the recycle gas source.

Amount of primary air: 750 l(S.T.P.)/h;

Amount of secondary air: 275 l(S.T.P.)/h;

Amount of recycle gas: 600 l(S.T.P.)/h; and

Chemical grade propylene: 77 l(S.T.P.)/h.

Amount of crude acrylic acid: 400 g/h.

Primary air, secondary air and chemical grade propylene are taken from compressed gas cylinders. The recycle gas is compressed and transported by means of a model compressor. The compression is effected from 0.1 bar gage pressure to 1.2 bar gage pressure (reactor entrance pressure).

Model compressor: One-stage radial compressor with half-closed rotor (it was also possible to use an open rotor of the same diameter without changing the result) having a diameter of 120 mm. Speed=1 200 revolutions per minute. Maximum delivery: 1.3 m$^3$(S.T.P.)/h.

b) COMPARATIVE EXAMPLE

As for the example, but the recycle gas compressor used is a three-stage axial compressor. The propeller diameter is 80 mm and the speed is 2 400 rpm. Maximum delivery: 1.3 m$^3$(S.T.P.)/h. The compression is likewise effected from 0.1 bar gage pressure to 1.2 bar gage pressure.

In contrast to the example, the comparative example has to be terminated after operation for about 5 weeks owing to considerable oscillations of the shaft and out-of-true running. This is due to polymeric acrylic acid deposits on the propeller.

Such deposits are to be found in about the same amount on the rotor of the radial compressor too but evidently do not have such a pronounced effect therein.

Corresponding deposits would form, for example by the deposition of impurities contained in fresh air, e.g. dust, etc., if the air supply is not from compressed gas cylinders but is effected by means of outside air as is usual on an industrial scale

We claim:

1. A process for the preparation of at least one organic compound by heterogeneously catalyzed partial gas-phase oxidation of at least one organic precursor compound in a reactor loaded with catalyst, in which at least one portion of the components of the reaction gas starting mixture is brought from a low initial pressure to a higher final pressure by means of a compressor, wherein the compressor used is a radial compressor.

2. The process as claimed in claim 1, wherein the at least one portion comprises air.

3. The process as claimed in claim 1, wherein the at least one portion contains at least one chemical compound having at least one ethylenically unsaturated double bond.

4. The process as claimed in claim 3, wherein the at least one chemical compound having at least one ethylenically unsaturated double bond is at least one member selected from the group consisting of acrolein, methacrolein, acrylic acid, methacrylic acid, acrylonitrile and methacrylonitrile.

5. The process as claimed in claim 1, wherein the heterogeneously catalyzed partial gas-phase oxidation is the partial oxidation of propylene to acrolein and/or acrylic acid or the partial oxidation of acrolein to acrylic acid.

6. The process as claimed in claim 1, wherein the heterogeneously catalyzed partial gas-phase oxidation is the partial oxidation of propane to acrylic acid.

7. The process as claimed in claim 1, wherein the heterogeneously catalyzed partial gas-phase oxidation is a partial ammoxidation.

8. The process as claimed in claim 1, wherein the at least one portion comprises recycle gas.

9. The process as claimed in claim 1, which is a heterogeneously catalyzed partial fixed-bed gas-phase oxidation of propene to acrylic acid, taking place in two successive steps, the propene space velocity of the fixed catalyst bed for the first step from propene to acrolein being $\geq 135$ l(S.T.P.) per l per h and the acrolein space velocity of the fixed catalyst bed for the second step from acrolein to acrylic acid being $\geq 125$ l(S.T.P.) per l per h.

10. The process as claimed in claim 9, the propene space velocity being $\geq 140$ l(S.T.P.) per l per h and the acrolein space velocity being $\geq 130$ l(S.T.P.) per l per h.

11. The process as claimed in claim 1, wherein the radial compressor is a gear radial compressor.

12. The process as claimed in claim 1, wherein the radial compressor is a multistage radial compressor.

13. The process is claimed in claim 1, wherein the radial compressor is a gear turbo radial compressor.

14. The process as claimed in claim 1, wherein the process is carried out at a temperature from 100 to 600° C.

15. The process as claimed in claim 1, wherein the at least one portion comprises at least one chemical compound having at least one ethylenically unsaturated double bond andior air.

16. The process as claimed in claim 1, wherein the at least one portion comprises reaction gas starting mixture and recycle gas and the compressor is a single radial compressor.

* * * * *